United States Patent [19]

Wu

[11] Patent Number: 4,935,551
[45] Date of Patent: * Jun. 19, 1990

[54] HYDROPEROXIDATION OF DIISOPROPYLBENZENE

[75] Inventor: Ching-Yong Wu, Pittsburgh, Pa.

[73] Assignee: Indspec Chemical Corporation, Pittsburgh, Pa.

[*] Notice: The portion of the term of this patent subsequent to Jul. 18, 2006 has been disclaimed.

[21] Appl. No.: 136,313

[22] Filed: Dec. 22, 1987

[51] Int. Cl.$^5$ ............................................. C07C 179/06
[52] U.S. Cl. ...................................... 568/562; 568/565
[58] Field of Search ................................. 568/562, 565

[56] References Cited

U.S. PATENT DOCUMENTS

| | | | |
|---|---|---|---|
| 2,632,772 | 3/1953 | Armstrong et al. | 260/610 |
| 3,883,600 | 5/1975 | Miller | 260/610 B |
| 3,911,020 | 10/1975 | Cooper | 568/565 |
| 3,928,469 | 12/1975 | Suda et al. | 568/565 |
| 3,953,521 | 4/1976 | Suda et al. | 260/610 B |
| 4,153,635 | 5/1979 | Wu et al. | 568/574 |
| 4,217,287 | 8/1980 | Wu et al. | 260/348.29 |
| 4,237,319 | 12/1980 | Nambu et al. | 568/571 |
| 4,271,321 | 6/1981 | Voges | 568/569 |
| 4,282,384 | 8/1981 | Wu et al. | 568/574 |
| 4,329,514 | 5/1982 | van der Weijst et al. | 568/565 |
| 4,670,609 | 6/1987 | Bennett et al. | 568/768 |

FOREIGN PATENT DOCUMENTS

| | | | |
|---|---|---|---|
| 58-88357 | 5/1983 | Japan | 568/565 |
| 727498 | 4/1953 | United Kingdom . | |

OTHER PUBLICATIONS

Tomita et al, *Chemical Abstracts*, vol. 89, No. 197168c (1978).
Journal of Catalysis 43, 380–383 (1976), "Selective Olefin Epoxidation at High Hydroperoxide-to-Olefin Ratios", pp. 380–383.
*Chemistry: Principles and Properties*, Michell J. Sienko & Robert A. Plane, pp. 371, 372 & 379.
Hackh's Chemical Dictionary, Julis Grant, p. 26.
"Introduction To Advanced Inorganic Chemistry", Philip John Durrant & Beryl Durrant, pp. 450 & 451.

*Primary Examiner*—Bruce D. Gray
*Attorney, Agent, or Firm*—Kirkpatrick & Lockhart

[57] ABSTRACT m-Diisopropylbenzene dihydroperoxide is produced in good yield in a continuous process by the oxidation of diisopropylbenzene, comprised of major amounts of the m-isomer and less than 6% of the o-isomer, under anhydrous, non-alkaline conditions with oxygen or air at about 85° C.–95° C.

3 Claims, 1 Drawing Sheet

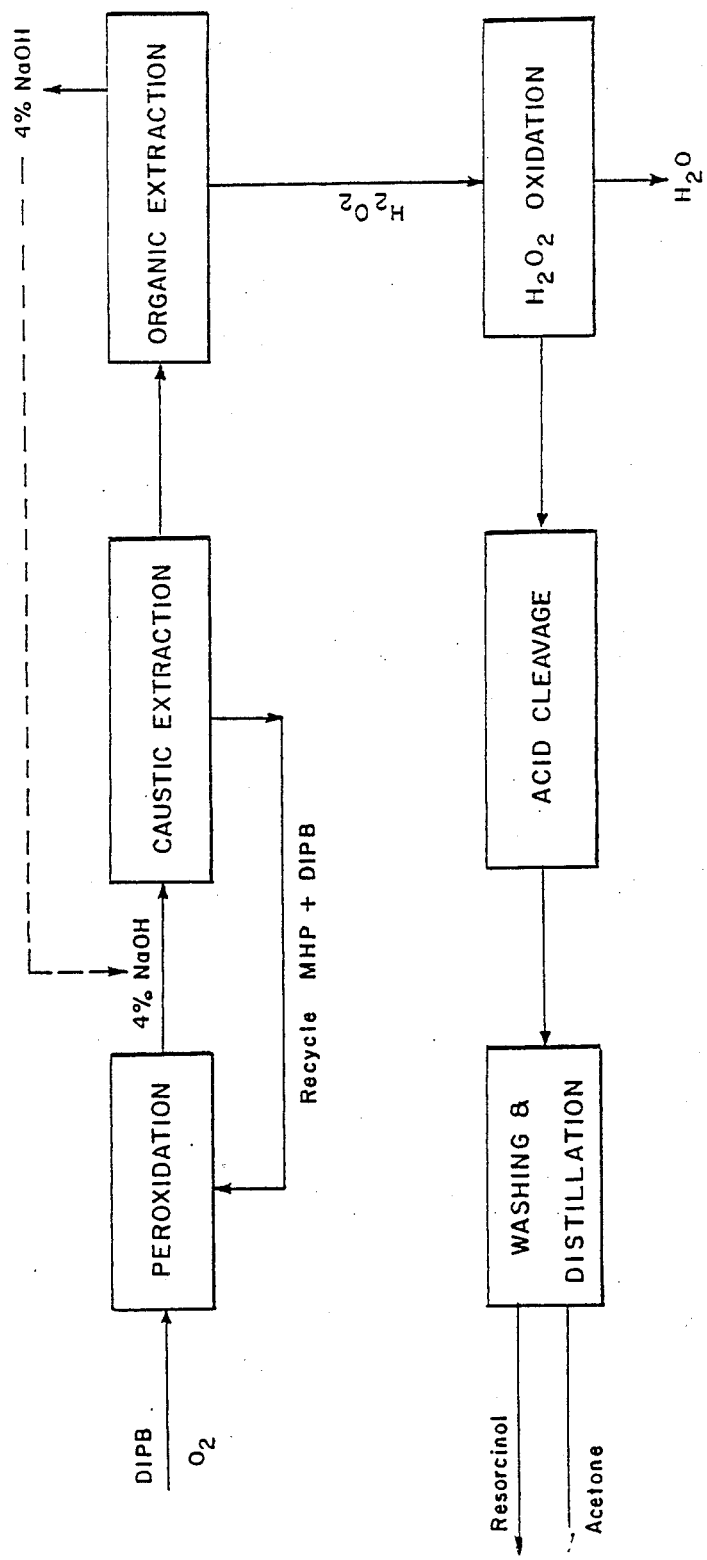

HYDROPEROXIDATION OF DIISOPROPYLBENZENE

BACKGROUND OF THE INVENTION

1. Field of the Invention

The present invention relates to a process for the production of the dihydroperoxides of alkylbenzenes, and more particularly, to the production of diisopropylbenzene dihydroperoxide in good yield.

2. Description of the Prior Art

The hydroperoxidation of diisopropylbenzene (DIPB) with oxygen or air under aqueous, alkaline conditions is known to produce numerous products in addition to the commercially desirable dihydroperoxides (DHP). Methods to obtain DHP without the formation of large amounts of co-products have been the object of research since 1947.

British Patent No. 727,498 which issued in 1953 describes the continuous oxidation of DIPB and the monohydroperoxide (MHP) under aqueous conditions in the presence of sodium hydroxide (NaOH) or ($Na_2CO_3$) until the MHP concentration is at least 45%. DHP is periodically or continuously extracted.

Another problem of the DIPB hydroperoxidation is the fact that it is also not easy to selectively produce DHP from (MHP). For example, when DIPB is oxidized in a batch reactor at 100° C. for eight hours, according to known hydroperoxidation methods, a 62% conversion of DIPB is obtained. However, the oxidation product contains more MHP (45%) than DHP (18%). Improved accuracy in analysis of hydroperoxidation by-products has revealed that the DHP production reported in some old literature is actually DHP and the hydroxyhydroperoxides (HHP). The combined yield of MHP and DHP is 86.6%. (See for example, Japan Kokai 78-68735). Although still further conversion leads to a decrease in MHP concentration and an increase in DHP concentration, the oxidation soon comes to a standstill (no more increase in peroxide concentration) before all MHP is converted to DHP and there is a considerable loss in oxidation selectivity. In other words, instead of converting DIPB to DHP, DIPB is converted to some by-products. Therefore, it is desirable to terminate the oxidation at the midpoint and to recover the unreacted feed material, DIPB and the intermediate product MHP, from the oxidation product solution, and to return them to the oxidation reactor after the resorcinol precursors (DHP and HHP) have been removed, instead of carrying out the oxidation until all DIPB is consumed. In such a continuous cyclic oxidation, the amount of DHP produced nearly equals the amount of DIPB consumed, and there is no net change in the concentrations of MHP in the feed and in the oxidation product. To meet this goal, assuming that the rate of DIPB oxidation to MHP equals the rate of MHP oxidation to DHP, one would tend to choose a feed containing about 1:1 ratio of DIPB and MHP for such a continuous cyclic oxidation. However, because of the presence of many side reactions which take place during the oxidation of a DIPB-MHP mixture, it is not always beneficial to keep the concentration of MHP near 50%. In fact, very good results have been obtained by keeping the concentration a little lower.

Sumitomo Chemical Company reported in Suda et al. U.S. Pat. No. 3,953,521 that m- and/or p-DHP are continuously produced by oxidizing the corresponding DIPB in liquid phase with air at 80° C. to 130° C., preferably 100° C., in the presence of an alkali as catalyst, while keeping the concentration of MHP in the oxidation product solution in the range of 20 to 40% by weight. The level of by-product formation was not disclosed in this patent. It was shown in a comparative example that using the same reactor, about 120 parts of DHP were obtained from 100 parts of DIPB when the MHP concentration was kept at 38%, whereas only 70 parts of DHP were obtained from 100 parts of MHP when the MHP concentration was about 50%. Theoretically, 140 parts DHP are produced from 100 parts DIPB.

It is well recognized from many investigations that the DHP recovered by extraction of the DIPB oxidation product with an aqueous sodium hydroxide solution usually contains from 25 to 35 wt % HHP. The Sumitomo patent did not disclose any information on HHP concentration either in the hydroperoxidation feed or in the hydroperoxidation product.

According to Japanese Patent No. 53-68735, issued to Sumitomo Chemical Company, when a recycle hydroperoxidation mixture containing 45.8% DIPB and 39.1% MHP was oxidized with air at 100° C. for five hours in the presence of 2% sodium hydroxide, a 71% yield to DHP and MHP was obtained.

This yield was 15% lower than the yield obtained when the oxidation was made with 100% DIPB under identical reaction conditions. No explanation was given for the lower yield. It suggests that in a cyclic hydroperoxidation process a lower yield of hydroperoxides can be expected. (See also Japan Kokai 58-88357).

Mitsui Petrochemical Industries'hydroperoxidation process is reported to be a noncyclic oxidation of DIPB. According to U.S. Pat. No. 4,237,319, a DHP-rich oxidation product was obtained by carrying out the oxidation of DIPB under alkaline conditions at a temperature in the range of 80° C. to 110° C., until the concentration of hydroperoxides at the end of the reaction reached at least 120 wt %, but less than 140 wt % (theoretical conversion of DIPB to DHP). The process coproduced a considerable amount of HHP and the dicarbinol (DCL) which must be converted to DHP in a separate reactor by an oxidation with hydrogen peroxide. Any unreacted DIPB and MHP were not recovered. Although the process eliminates the need to separate DHP by a caustic extraction followed by another extraction with an organic solvent, the values of DHP/DHP+HHP+DCL are calculated to be 71 to 73%. The mol % yield to DHP+HHP+DCL was reported in the range of 79 to 83%. It is estimated that the overall yield of Mitsui Petrochemical Industries'- process for converting DIPB to DHP is not more than 75-80%. (See also Japan Kokai 61-180764).

A method of preparing diisopropylbenzene hydroperoxides under substantially anhydrous conditions in the presence of minute quantities of a barium oxide catalyst at temperatures between about 70° C. and about 130° C. is disclosed in Wu et al. U.S. Pat. No. 4,282,384.

A method for producing hydroquinone is known which includes the step of continuously oxidizing p-DIPB under nonalkaline conditions with oxygen or air at 83°-87° C. The mol % p-DIPB in the oxidate is 26%. Other products include DHP and MHP.

Additional hydroperoxidation methods are disclosed in Voges U.S. Pat. No. 4,271,321 and Miller U.S. Pat. No. 3,883,600.

An object of the present invention is to provide a method of oxidizing diisopropylbenzene with improved selectivity for the dihydroperoxide. A further object of the present invention is to improve the production of the m-isomer of diisopropylbenzene dihydroperoxide.

SUMMARY OF THE INVENTION

The objects of the present invention are achieved by a process in which diisopropylbenzene, comprised of m-diisopropylbenzene diisopropylbenzene and less than 6% o-diisopropylbenzene, is oxidized under anhydrous, non-alkaline conditions with oxygen or air at about 85° C.-95° C. in a continuous process. The hydroperoxidation method of the present invention produced a 92.8% yield of m-diisopropylbenzene dihydroperoxide (m-DHP) and m-diisopropylbenzene hydroxyhydroperoxide (m-HHP), of which approximately 75% was m-DHP and 25% was m-HHP. Furthermore, the composition remains substantially the same through at least ten cycles of batch operations.

BRIEF DESCRIPTION OF THE FIGURE

The FIGURE is a schematic illustration of the process of the present invention.

In prior art hydroperoxidation processes, DIPB is oxidized in a pressurized reactor with either air or molecular oxygen in the presence of sufficient dilute aqueous sodium hydroxide to maintain the pH between 7 and 9. In the present invention, the oxidation of DIPB with oxygen is carried out without using dilute aqueous sodium hydroxide.

In the prior art hydroperoxidation processes, m-DIPB is reacted with oxygen in the liquid phase at 80° to 130° C. In commercial scale processes the reaction is run at temperatures in the upper portion of the range, 95° to 100° C. The higher temperatures in turn require higher pressure to prevent evaporation. Here m-DIPB is oxidized first to monohydroperoxide (MHP) which in turn is oxidized to dihydroperoxide (DHP). Since both MHP and DHP are thermally unstable under the peroxidation conditions, at higher temperatures many other products are also formed. In the initial stages of the oxidation, MHP is the main product because the concentration of DIPB is much greater than MHP. While being oxidized to DHP, MHP can also give up one oxygen atom to form a monocarbinol (MCL, isopropylphenyldimethyl carbinol) which in turn can be oxidized to hydroxyhydroperoxide (HHP), as follows:

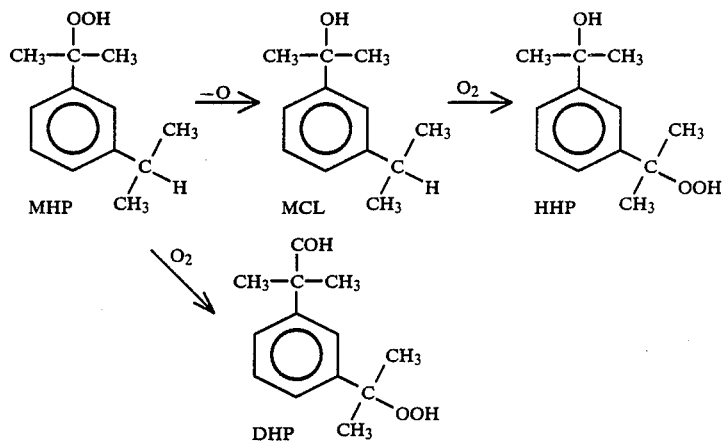

DETAILED DESCRIPTION OF THE PREFERRED EMBODIMENT

In the process of the present invention, shown schematically in the FIGURE, a feed stream, comprised of major amounts of m-DIPB and less than about 6% o-DIPB is oxidized with oxygen or air in a nonaqueous, non-alkaline system at about 85° C.-95° C. The hydroperoxidation product is extracted with dilute aqueous sodium hydroxide to separate the DHP/HHP fraction as in the Sumitomo process. About 80% of the remaining hydroperoxidation products, including the MHP/unreacted DIPB fraction is recycled to the feed stream for further hydroperoxidation. The aqueous sodium hydroxide solution is extracted back with an organic solvent, such as hot MIBK, to recover the DHP/HHP product. The DHP/HHP product is then preferably treated by any suitable known method to convert most of the HHP to DHP without decomposing DHP. Finally the DHP is decomposed to resorcinol and acetone by any suitable method. The decomposition product is finally purified by any suitable means, such as neutralizing with dilute sodium hydroxide and distilling to obtain resorcinol.

At the same time, smaller amounts of the corresponding monoketone (MKT) and ketone hydroperoxide (KHP) are formed, by splitting off methanol from MHP and DHP, respectively. The KHP can lose another molecule of methanol to form a diketone (DKT, 1,3-diacetylbenzene).

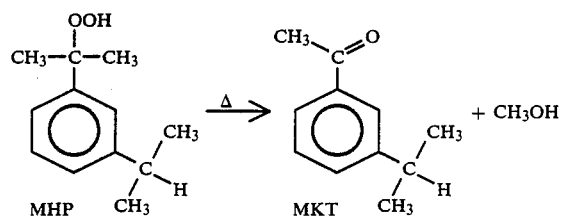

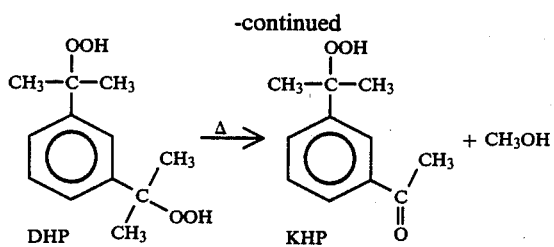

At the temperature employed in the prior art systems for the oxidation of DIPB (80°–130° C.), the ratio of ketone formation to carbinol formation is roughly 1 to 3. Finally, the HHP may lose an oxygen atom to form a dicarbinol (DCL). All the products mentioned above have been found in the oxidation product of m-DIPB. However, the three products present in the largest amount are MCL, DCL and diisopropylbenzene olefin carbinol (OLCL), which are formed by dehydration of DCL.

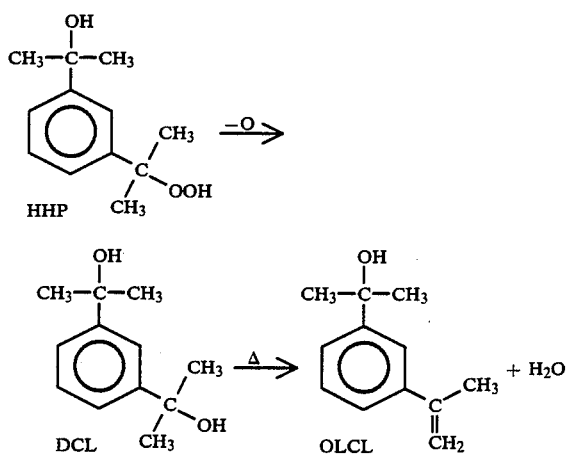

EXAMPLE 1

Hydroperoxidation Under Anhydrous, Non-Alkaline Conditions

Table I shows the analysis of products from the hydroperoxidation of CP grade m-DIPB in a nonaqueous, nonalkaline medium.

Hydroperoxidation was made in a one-liter 3-neck flask equipped with a stirrer, thermometer, reflux condenser, and gas-bubbler. The reaction mixture in the flask was stirred and heated to the desired temperature with a heating mantle while approximately 100 ml/min. oxygen was bubbled through the reaction mixture.

In the initial hydroperoxidation, when no recycle m-MHP/m-DIPB was used, 700 g CP grade m-DIPB and 30 g initiator, which was a 51% m-MHP/m-DIPB mixture, were used as the starting material. In the subsequent recycle experiments (Recycle Runs 1 to 9), the recycle m-MHP/m-DIPB fraction (usually about 650 g) was mixed with enough fresh m-DIPB to make 750 g of starting material.

During the hydroperoxidation, a small sample (0.5 g) was removed from the reaction mixture every four hours and titrated iodometrically to determine total peroxide concentration expressed as % MHP.

$$\% MHP = \frac{[\text{ml } 0.1 \text{ N Na}_2\text{S}_2\text{O}_3 \text{ solution}][0.1][MWMHP] \times 100}{[\text{Sample weight, g}] \times 2 \times 1000}$$

Hydroperoxidation was terminated when the titrated % MHP value reached about 75%–80%, which normally took about 16 to 24 hours.

The DHP/HHP product was obtained by extracting the hydroperoxidation product with dilute aqueous alkaline solution. The remaining organic phase, which contained about a 2:1 ratio of MHP/DIPB, was recycled. In the cyclic hydroperoxidation, the recycle MHP/DIPB was mixed with fresh DIPB equivalent to the amount of DHP/HHP product removed in order to maintain the same moles of MHP and DIPB throughout the cyclic process. In the actual operation, a constant weight of hydroperoxidation feed was charged in all 9 cycles of hydroperoxidation to meet this requirement.

TABLE I

DHP/HHP from CP m-DIPB, 100% Recycle

| Recycle No. | Conditions | | MHP,[1] % | DHP/HHP | | MHP/DIPB Recycle | |
|---|---|---|---|---|---|---|---|
| | time hrs | temp. °C. | | wt, g | DHP,[1] % | wt, g | MHP,[1] % |
| 0 | 32 | 82–88 | 73.3 | 161.0 | 89.5 | 674 | 54.9 |
| 1 | 16 | 84–85 | 75.4 | 100.3 | 85.5 | 685 | 59.7 |
| 2 | 16 | 83–85 | 75.9 | 96.5 | 83.6 | 661 | 61.6 |
| 3 | 16 | 84–85 | 77.9 | 126.4 | 87.8 | 648 | 62.2 |
| 4 | 24 | 85 | 86.2 | 183.0 | 86.1 | 613 | 56.6 |
| 5 | 24 | 85–86 | 76.5 | 84.3 | 88.2 | 663 | 62.9 |
| 6 | 24 | 85–90 | 77.7 | 128.0 | 84.7 | 651 | 56.1 |
| 7 | 24 | 83–87 | 73.5 | 79.5 | 82.2 | 690 | 61.6 |
| 8 | 24 | 85–91 | 75.7 | 83.8 | 81.0 | 697 | 63.7 |
| 9 | 24 | 87–93 | 71.6 | 77.0 | 73.6 | 708 | 59.4 |
| Av. 1–9 | | | 76.7 | 106.5 | 83.6 | 668 | 60.4 |

| | | | | Net Production[2] | | |
|---|---|---|---|---|---|---|
| Recycle No. | Conditions | | DIPB Conv.[2,3] % | DHP Mol % | HHP Mol % | DHP/ DHP + HHP % |
| | time hrs. | temp. °C. | | | | |
| 0 | 32 | 82–88 | 66.3 | 14.8 | 1.7 | 89.7 |
| 1 | 16 | 84–85 | 43.5 | — | — | — |
| 2 | 16 | 83–85 | — | 9.0 | 2.7 | 76.9 |
| 3 | 16 | 84–85 | 41.7 | 12.5 | 2.2 | 85.0 |
| 4 | 24 | 85 | 53.4 | 17.2 | 2.2 | 88.7 |
| 5 | 24 | 85–86 | 48.8 | 8.0 | 2.6 | 75.5 |
| 6 | 24 | 85–90 | 43.6 | 9.9 | 2.7 | 78.6 |
| 7 | 24 | 83–87 | 40.8 | 7.9 | 2.5 | 76.0 |
| 8 | 24 | 85–91 | 35.1 | 7.4 | 3.8 | 66.1 |
| 9 | 24 | 87–93 | 32.6 | 4.6 | 4.2 | 52.2 |
| Av.1–9 | | | 42.4 | 8.5 | 2.5 | 77.0 |

[1]By iodometric titration.
[2]Calculated from high performance liquid chromatographic analysis (HPLC).
[3]These conversions were calculated from data obtained under variable caustic extraction conditions.

Columns 2, 4, and 6 of Table I represent results of iodometric titration expressed as wt % MHP, DHP, and MHP, respectively. The iodometric titration determines the amount of active oxygen in the sample which is calculated as though it were a single hydroperoxide. It cannot be used to distinguish different hydroperoxides.

Data shown in columns 8, 9, and 10 of Table I were obtained by high performance liquid chromatographic (HPLC) analysis. They show the net conversion of DIPB and net production of DHP and HHP (as mol %) for each cycle of hydroperoxidation. The last line of Table I shows the average values for cycles 1 to 9.

A quantitative determination of a mixture of hydroperoxides was made by HPLC analysis. Pure samples of DHP, MHP, DCL, OLCL, DKT, MCL, MKT, and HHP were used for the calibration of HPLC data. The results are shown in Table II.

TABLE II

Composition of Product From Hydroperoxidation of CP m-DIPB

| | DCL | OLCL | DKT | HHP | DHP | MCL | MHP | MKT | DIPB |
|---|---|---|---|---|---|---|---|---|---|
| Recycle 0 | | | | | | | | | |
| Product | 0.4 | 0.3 | <0.1 | 1.7 | 14.8 | 8.2 | 40.0 | 1.1 | 33.7 |
| Net Prodn. | 0.4 | 0.3 | <0.1 | 1.7 | 14.8 | 8.2 | 40.0 | 1.1 | −66.3 |
| Recycle 1 and 2 | | | | | | | | | |
| Product | 0.4 | 0.5 | <0.1 | 2.7 | 9.0 | 9.8 | 48.1 | 1.5 | 27.9 |
| Charge | 0.3 | 0.2 | 0 | 0.5 | 1.4 | 7.8 | 39.3 | 1.1 | 49.4 |
| Net Prodn. | 0.1 | 0.3 | <0.1 | 2.2 | 7.6 | 2.0 | 8.8 | 0.4 | −21.5 |
| Recycle 3 | | | | | | | | | |
| Product | 0.6 | 0.7 | <0.1 | 3.0 | 13.6 | 10.2 | 45.6 | 1.6 | 24.6 |
| Charge | 0.3 | 0.4 | 0 | 0.8 | 1.1 | 9.1 | 44.7 | 1.4 | 42.2 |
| Net Prodn. | 0.3 | 0.3 | <0.1 | 2.2 | 12.5 | 1.1 | 0.9 | 0.2 | −17.6 |
| Recycle 4 | | | | | | | | | |
| Product | 0.7 | 0.8 | <0.1 | 3.5 | 19.7 | 9.9 | 42.3 | 1.6 | 21.5 |
| Charge | 0.5 | 0.6 | 0 | 1.3 | 2.5 | 8.7 | 39.0 | 1.5 | 46.1 |
| Net Prodn. | 0.2 | 0.2 | <0.1 | 2.2 | 17.2 | 1.2 | 3.3 | 0.1 | −24.6 |
| Recycle 5 | | | | | | | | | |
| Product | 0.9 | 2.0 | <0.1 | 3.9 | 10.6 | 13.3 | 45.1 | 1.3 | 22.9 |
| Charge | 0.6 | 0.7 | 0 | 1.3 | 2.6 | 9.0 | 39.6 | 1.5 | 44.7 |
| Net Prodn. | 0.3 | 1.3 | 0.1 | 2.6 | 8.0 | 4.3 | 5.5 | −0.2 | −21.8 |
| Recycle 6 | | | | | | | | | |
| Product | 1.1 | 2.0 | <0.1 | 4.2 | 10.6 | 12.7 | 41.0 | 1.1 | 27.2 |
| Charge | 0.7 | 1.2 | 0 | 1.5 | 0.7 | 10.1 | 36.7 | 0.9 | 48.2 |
| Net Prodn. | 0.4 | 0.8 | <0.1 | 2.7 | 9.9 | 2.6 | 4.3 | 0.2 | −21.0 |
| Recycle 7 | | | | | | | | | |
| Product | 1.1 | 2.3 | <0.1 | 4.8 | 10.6 | 12.1 | 43.2 | 1.5 | 24.4 |
| Charge | 1.0 | 2.1 | 0.02 | 2.3 | 2.7 | 11.8 | 37.7 | 1.2 | 41.2 |
| Net Prodn. | 0.1 | 0.2 | <0.08 | 2.5 | 7.9 | 0.3 | 5.5 | 0.3 | −16.8 |
| Recycle 8 | | | | | | | | | |
| Product | 1.8 | 3.5 | 0.05 | 7.3 | 11.0 | 12.3 | 40.3 | 1.6 | 22.2 |
| Charge | 0.9 | 2.8 | 0 | 3.5 | 3.6 | 11.8 | 42.8 | 1.5 | 34.2 |
| Net Prodn. | 0.9 | 0.7 | 0.05 | 3.8 | 7.4 | 0.5 | −2.5 | 0.1 | −12.0 |
| Recycle 9 | | | | | | | | | |
| Product | 2.7 | 5.1 | 0.1 | 9.5 | 8.8 | 13.6 | 35.5 | 1.9 | 23.0 |
| Charge | 1.5 | 3.1 | 0 | 5.3 | 4.2 | 11.8 | 38.5 | 1.6 | 34.1 |
| Net Prodn. | 1.2 | 2.0 | 0.1 | 4.2 | 4.6 | 1.8 | −3.0 | 0.3 | −11.1 |
| Recycle 1–9 | | | | | | | | | |
| Tot. Prodn. | 3.5 | 5.8 | 0.7 | 22.4 | 75.1 | 13.8 | 22.8 | 1.4 | −146.4 |

Referring again to Example 1 and Table I, after 10 hydroperoxidation cycles, a total of 1120 g DHP/HHP product was obtained. From the HPLC data, it was calculated that for the nine cyclic operations the average mol % DHP in DHP+HHP product stream was 77%, excluding a small fraction of MHP which was also extracted into the product stream and should be removed from the product stream. It was also found that the average DIPB conversion was 42.4%. The ratio of product (DHP+HHP) v. recycle (MHP+DIPB) was 106.5:668–1:6.3 for the nine recycles. These values are low compared to those obtained in subsequent experiments using commercial m-DIPB. Based on subsequent work, described in Table IX below, for a 50% DIPB conversion, a ratio of 1:4 can be expected.

EXAMPLE 2

Hydroperoxidation Under Aqueous, Alkaline Conditions

In order to compare the results of Example 1 with aqueous, alkaline hydroperoxidation processes, four hydroperoxidation runs of CP m-DIPB in the presence of 2% aqueous sodium hydroxide solution were made using the same equipment. The results are shown in Table III. A pressure reactor was not used. Therefore, the experiments were limited to 1 atm and 100° C. The present commercial processes are believed to use higher temperatures and higher pressure.

The same one-liter flask was used for the hydroperoxidation of 600 g CP m-DIPB containing 30 g 56% m-MHP as initiator, in the presence of 65 g 2% aqueous sodium hydroxide. The subsequent hydroperoxidation with recycled MHP-DIPB was made with 650 g charge consisting of recycle MHP-DIPB and additional fresh m-DIPB.

The reaction temperature was raised to 95–100° C. because the hydroperoxidation was much slower than in nonaqueous, non-alkaline media. The use of greater than 1 atm and higher than 100° C. was avoided in order to obtain data comparable with the data from nonaqueous hydroperoxidation.

Generally the same work-up procedure as described above was used. After the hydroperoxidation experiment of Recycle 0, the aqueous layer was separated and the products from the experiments with equal weights of 10% aqueous sodium hydroxide. The products from the experiments of Recycles 1 and 2 were extracted with equal weights of 4% aqueous sodium hydroxide. Extraction with 10% sodium hydroxide is more complete and has produced a MHP/DIPB recycle containing less DHP/HHP product. The composition of the hydroperoxidation products was calculated as before and shown in Table IV.

TABLE III
DHP/HHP from CP m-DIPB in the Presence of Sodium Hydroxide

| Recycle No. | Conditions time hrs. | Conditions temp. °C. | MHP[1] % | DHP/HHP wt g | DHP/HHP DHP[1] % | MHP/DIPB Recycle wt g | MHP/DIPB Recycle MHP[1] % | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|
| 0 | 36 | 90–99 | 58.0 | 87.0 | 79.7 | 595 | 43.8 | 63.1 | 6.5 | 4.9 | 57.0 |
| 1 | 28 | 95–100 | 59.0 | 93.6 | 75.7 | 542 | 47.4 | 45.4 | 5.9 | 6.5 | 47.6 |
| 2 | 32 | 99 | 54.0 | 83.9 | 64.9 | 569 | 42.7 | 44.3 | 3.2 | 6.4 | 33.3 |
| 3 | 32 | 100 | 45.2 | 56.6 | 67.4 | 453 | 36.1 | 35.6 | 3.2 | 3.0 | 51.6 |
| Av. 1–3 | | | 52.7 | 78.0 | 69.3 | 521 | 42.1 | 41.8 | 4.10 | 5.30 | 43.6 |

[1] By iodometric titration.
[2] Calculated from HPLC analysis.

TABLE IV
Hydroperoxidation Products From CP m-DIPB in the Presence of 2% NaOH

| | COMPONENTS, Mol % | | | | | | | | |
|---|---|---|---|---|---|---|---|---|---|
| | DCL | OLCL | DKT | HHP | DHP | MCL | MHP | MKT | DIPB |
| Recycle 0 | | | | | | | | | |
| Product | 0.6 | 2.0 | <0.1 | 4.9 | 6.5 | 11.9 | 36.2 | 1.0 | 36.9 |
| Net Prodn. | 0.6 | 2.0 | <0.1 | 4.9 | 6.5 | 11.9 | 36.2 | 1.0 | −63.1 |
| Recycle 1 | | | | | | | | | |
| Product | 1.7 | 4.7 | <0.1 | 8.0 | 6.7 | 15.8 | 33.8 | 2.0 | 27.3 |
| Charge | 0.5 | 1.7 | 0 | 1.5 | 0.8 | 11.0 | 33.5 | 1.0 | 50.0 |
| Net Prodn. | 1.2 | 3.0 | <0.1 | 6.5 | 5.9 | 4.8 | 0.3 | 1.0 | −22.7 |
| Recycle 2 | | | | | | | | | |
| Product | 2.4 | 8.6 | <0.1 | 9.6 | 3.7 | 18.3 | 28.7 | 2.9 | 25.7 |
| Charge | 1.2 | 3.9 | 0 | 3.2 | 0.5 | 13.9 | 29.4 | 1.7 | 46.1 |
| Net Prodn. | 1.2 | 4.7 | <0.1 | 6.4 | 3.2 | 4.4 | −0.7 | 1.2 | −20.4 |
| Recycle 3 | | | | | | | | | |
| Product | 4.0 | 10.8 | <0.1 | 6.7 | 3.7 | 23.3 | 25.1 | 3.5 | 22.8 |
| Charge | 1.9 | 7.5 | 0 | 3.5 | 0.7 | 17.9 | 30.2 | 2.9 | 35.4 |
| Net Prodn. | 2.1 | 3.3 | <0.1 | 3.2 | 3.0 | 5.4 | −5.1 | 0.6 | −12.6 |

Comparing the data of Tables I and III, it is apparent that the hydroperoxidation of m-DIPB in an anhydrous, non-alkaline media is better in many aspects than hydroperoxidation in the presence of dilute aqueous sodium hydroxide. First, the average final hydroperoxide concentration, calculated as wt % MHP from iodometric titrations was 76.7% for the nine cycles of nonaqueous hydroperoxidation, whereas the corresponding value for the three cycles in the presence of 2% aqueous sodium hydroxide was 52.7%. Second, the average % DHP of the DHP/HHP fraction, determined by iodometric titration, was 83.6% for the former and 69.3% for the latter. The value of DHP/DHP+HHP was 77.0% and 43.6%, respectively. It is concluded that hydroperoxidation in nonaqueous, non-alkaline media gives higher conversion of m-DIPB and better selectivity to the desired product. Comparing the hydroperoxidation of Recycle 0 (pure DIPB oxidation), the caustic extraction produced 87.0 g DHP/HHP fraction v. 161.0 g for the nonaqueous system. For the first three recycles, the average DHP/HHP product weighed 78.0 g v. 107.7 g for the nonaqueous system. In the oxidation process, the addition of water slows the process. It appears that the hydroperoxidation of m-DIPB in the presence of aqueous sodium hydroxide does in fact take place at a much slower rate than the hydroperoxidation in nonaqueous media.

Since hydroperoxidation of DIPB in the presence of aqueous sodium hydroxide is a slower reaction compared to that of the nonaqueous system, it would be expected to produce a lower quality DHP/HHP fraction. This, indeed, was observed. The average selectivity of DHP/HHP product from the aqueous sodium hydroxide runs was 43.6 mol % compared to 77.0 mol % for the nonaqueous system.

A possible, although somewhat over-simplified explanation of the results can be made as follows:

In the hydroperoxidation of DIPB to DHP, most of the DHP is produced in the chain propagation step of

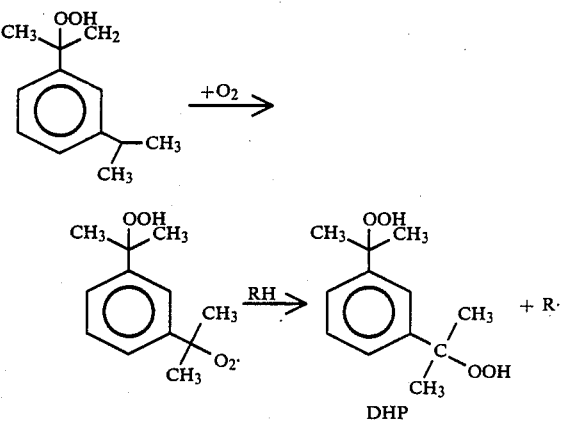

On the other hand, some HHP is produced from decomposition of DHP, e.g.,

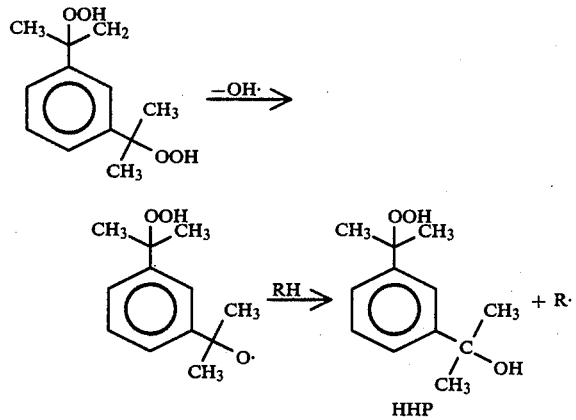

In the fast oxidation of DIPB, the chain propagation takes place rapidly and the production of DHP is favored. Only when the oxidation is slowed down, the decomposition of DHP becomes competitive, resulting in the production of more HHP.

As the concentration of HHP in the hydroperoxidation mixture increases, it can decompose to form secondary products, such as DCL and OLCL.

In order to compensate for the slower hydroperoxidation, commercial prior art processes employ higher reaction temperature and pressure, which in turn produce more by-products.

The nonaqueous hydroperoxidation process of the present invention permits operation at a lower reaction temperature, ideally about 85° C., and at a lower pressure, to achieve a high product selectivity. The oxidation process of the present invention can therefore be run in an open system without concern for pressure reaction vessels.

The process of the present invention produces its best results when the DIPB in the feed stream is comprised of major amounts of m-DIPB and less than about 6% o-DIPB. Commercially available DIPB, manufactured by alkylating benzene with propylene, usually contains all three isomers (o, m, and p). Since it is difficult to separate o-DIPB from m-DIPB by fractional distillation, it is important to determine the amount of the o-isomer tolerable in the DIPB feed.

Synthetic feeds of m-DIPB containing 2.5% and 5% o-DIPB were prepared and used in the cyclic hydroperoxidation study. Tables V and VI show the results of those experiments.

EXAMPLE 3

Hydroperoxidation of m-DIPB Containing 2.5% o-DIPB

Hydroperoxidation of 750 g m-DIPB containing 2.5% o-DIPB was made in a one-liter flask at 85-88° C. and 1 atm in nonaqueous, non-alkaline media using the same procedure as described earlier. In all experiments products were extracted once with an equal weight of 4% aqueous sodium hydroxide to separate the DHP/HHP fraction. The aqueous sodium hydroxide solution was extracted once with twice its weight and once with an equal weight of MIBK at 80° C. to recover the DHP/HHP fraction. Again, both the product and the recycle MHP/DIPB were analyzed by HPLC to determine their composition.

EXAMPLE 4

Hydroperoxidation of m-DIPB Containing 5% o-DIPB

Hydroperoxidation of 350 g m-DIPB containing 5% o-DIPB was made in a 500-ml flask at 85-92° C. and 1 atm in nonaqueous, non-alkaline media for a period of about 24 hours, until the peroxide concentration was about 50-70% MHP. The product was extracted once with an equal weight of 4% aqueous sodium hydroxide. The aqueous sodium hydroxide solution containing the sodium salts of DHP and HHP was extracted twice at 80° C. with twice its volume of MIBK to isolate the DHP/HHP product. After evaporation of MIBK, the residue was analyzed by HPLC to determine its DHP/HHP content.

TABLE V

| | | | | | | | | | | |
|---|---|---|---|---|---|---|---|---|---|---|
| | DHP/HHP from m-DIPB Containing 2.5% o-DIPB, 100% Recycle | | | | | | | | | |
| | Conditions | | | DHP/HHP | | MHP/DIPB Recycle | | DIPB | Net Production[2] | | |
| Recycle No. | time hrs. | temp. °C. | MHP[1] % | wt g | DHP[1] % | wt g | MHP[1] % | Conv.[2] % | DHP Mol % | HHP Mol % | DHP/DHP + HHP % |
| 0 | 32 | 85–89 | 71.3 | 98.0 | 83.0 | 712 | 61.3 | 62.2 | 11.7 | 2.0 | 85.4 |
| 1 | 16 | 85–87 | 77.3 | 85.7 | 86.9 | 686 | 64.0 | 31.5 | 7.7 | 2.1 | 78.6 |
| 2 | 16 | 85–87 | 72.5 | 86.0 | 82.4 | 660 | 64.1 | 25.6 | 6.3 | 1.7 | 78.7 |
| 3 | 24 | 85–87 | 74.7 | 82.5 | 79.9 | 668 | 62.8 | 38.0 | 6.9 | 3.0 | 69.7 |
| 4 | 24 | 87–88 | 72.4 | 79.0 | 79.6 | 678 | 63.5 | 32.1 | 6.5 | 2.6 | 71.4 |
| 5 | 24 | 87 | 71.6 | 80.0 | 76.8 | 650 | 60.2 | 34.1 | 6.1 | 3.4 | 64.2 |
| 6 | 24 | 85–88 | 63.1 | 69.1 | 70.9 | 677 | 55.6 | 29.8 | 4.1 | 2.2 | 65.1 |
| 7 | 24 | 86–87 | 58.9 | 67.2 | 67.3 | 658 | 50.9 | 30.8 | 3.4 | 2.5 | 57.6 |
| 8 | 24 | 87–89 | 55.2 | 62.4 | 64.7 | 666 | 47.4 | 35.8 | 3.4 | 2.4 | 58.6 |
| 9 | 24 | 87–88 | 53.5 | 61.2 | 63.7 | 673 | N.D.[3] | 47.7 | 2.8 | 4.1 | 40.6 |
| 10 | 24, | 87–88 | 55.0 | 59.8 | 63.1 | 664 | 44.9 | 46.9 | 2.7 | 2.3 | 54.0 |
| Av. 1–10 | | | 65.4 | 73.3 | 73.5 | 668 | 57.0 | 35.2 | 4.99 | 2.63 | 65.5 |

[1]By iodometric titration.
[2]Calculated from HPLC analysis.
[3]Not determined.

TABLE VI

DHP/HHP from m-DIPB Containing 5.0% o-DIPB, 100% Recycle

| Recycle No. | Conditions time hrs. | Conditions temp. °C. | MHP % | DHP/HHP wt g | DHP/HHP DHP[1] % | MHP/DIPB Recycle wt g | MHP/DIPB Recycle MHP[1] % | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|
| 0 | 40 | 80–96 | 75.4 | 47.6 | 80.7 | 305 | 60.3 | 67.0 | 11.2 | 7.8 | 59.0 |
| 1 | 24 | 85–91 | 64.3 | 30.5 | 80.0 | 338 | 59.9 | 37.8 | 5.4 | 3.7 | 59.3 |
| 2 | 24 | 85–92 | 71.7 | 40.6 | 74.1 | 269 | 61.2 | 43.6 | 6.1 | 3.8 | 61.6 |
| 3 | 24 | 88–92 | 59.4 | 32.8 | 68.8 | 273 | 51.5 | 38.9 | 3.5 | 2.9 | 54.7 |
| 4 | 24 | 87–90 | 53.4 | 34.1 | 62.7 | 269 | 43.9 | 41.3 | 3.1 | 1.1 | 73.8 |
| 5 | 32 | 86–90 | 52.9 | 32.4 | 63.9 | 276 | 43.2 | 43.0 | 3.3 | 2.4 | 57.9 |
| Av. 1–5 | | | 60.3 | 34.1 | 69.9 | 285 | 51.9 | 40.9 | 4.28 | 2.78 | 60.6 |

[1] By iodometric titration.
[2] Calculated from HPLC analysis.

Comparison of the data in Tables V and VI with the data in Table I shows that:

(1.) Final hydroperoxide concentrations determined by iodometric titration are 10–15% higher in the cases of CP grade m-DIPB.

(2.) The DHP/HHP fractions obtained by caustic extraction contain less DHP (% DHP by titration) in the experiments with m-DIPB containing 2.5% and 5% o-DIPB. The average % DHP by titration was 83.6% for CP grade m-DIPB, 73.5% for m-DIPB containing 2.5% o-DIPB and 69.9% for m-DIPB containing 5% o-DIPB.

(3.) The CP grade m-DIPB runs gave highest % DHP/DHP+HHP values (average 77%) than the runs containing o-DIPB (65.5% and 60.6%, respectively). Analysis of the hydroperoxidation by-products revealed that the presence of o-DIPB in DIPB feed increases the production of by-products, such as OLCL and MKT. The average mol % OLCL and MKT in the hydroperoxidation products of CP DIPB were 0.61% and 0.25%, respectively. The corresponding values with DIPB containing 5% o-DIPB were 2.75% and 0.58%, respectively.

It can be concluded, therefore, that a higher percentage of o-DIPB in the m-DIPB feed not only reduces the rates of m-DIPB hydroperoxidation, but also decreases the selectivity to the desirable products m-DHP and m-HHP.

EXAMPLE 5

Hydroperoxidation of m-DIPB Containing Large Percentages of o-DIPB

The same procedure was used to hydroperoxidate m-DIPB containing 10%, 26%, 38%, and 43% o-DIPB, respectively, in the initial feed. The procedures were the same as those described for m-DIPB containing 5% o-DIPB, except that the percentage content of o-DIPB was altered accordingly. Technical grade DIPB containing 26% o-DIPB used in one experiment yielded recovered DIPB containing 38% o-DIPB which was used in another experiment. The recovered DIPB from the first recycle hydroperoxidation of the run containing 38% o-DIPB was found to contain 43% o-DIPB and was used as the charge for yet another experiment.

Hydroperoxidation of m-DIPB containing 10% and 26% o-isomer failed to produce satisfactory yields of m-DHP, even after only one recycle. There was a significant increase in the production of undesirable by-products, including DCL, OLCL, and MKT. It took 64 hours (twice as long as standard experiments) to obtain a 41% m-DIPB conversion when m-DIPB containing 26% o-isomer was used. In a similar experiment using m-DIPB containing 38% o-isomer, the DIPB conversion was only 26% after 64 hours. It was not possible to carry out the hydroperoxidation of the MHP/DIPB recycles from these two experiments. There was no increase in hydroperoxide concentration when the MHP/DIPB recycle obtained from the hydroperoxidation of m-DIPB containing 38% o-DIPB was heated at 85° C. in the presence of oxygen. The hydroperoxidation products from these two runs contained higher concentrations of by-products than the desirable DHP/HHP products, indicating a significant decomposition of DHP, HHP, and probably even MHP.

From the data it has been determined that when the percentage of o-isomer in DIPB exceeds about 6%, hydroperoxidation of DIPB becomes increasingly difficult under the same experimental conditions.

Additional experiments revealed that the hydroperoxidation of p-DIPB in nonaqueous, non-alkaline media behaved differently than the hydroperoxidation of m-DIPB. Hydroperoxidation of 100% p-DIPB under the conditions of the present invention showed no improvement over the yields of the prior art aqueous, alkaline hydroperoxidation processes. Moreover, and surprisingly, when the oxidation by-products, p-MHP/p-DIPB, were recycled to the feed stream for further hydroperoxidation, no hydroperoxides were produced under anhydrous, non-alkaline conditions.

Because o-DIPB is not oxidized during the hydroperoxidation of m-DIPB, it accumulates in the unreacted DIPB stream and the concentration of o-DIPB increases with the number of recycles of the DIPB.

It is generally recognized that it would be unrealistic to expect a commercial DIPB feed containing less than 1% o-isomer. Therefore, it is necessary to return a portion of the unreacted DIPB containing a higher percentage o-DIPB from the recycle stream and send it back to the alkylation plant for isomerization in order to prevent the build-up of o-DIPB which causes poor hydroperoxide yield. This can be done either by diverting a portion of recycle DIPB after each recycle or by displacing all unreacted DIPB after several recycles.

EXAMPLE 6

Hydroperoxidation of m-DIPB Containing 1.2% o-DIPB with an 80% Recycle of Recovered m-MHP and m-DIPB Hydroperoxidation of m-DIPB containing 1.2% o-DIPB was made using the same procedure as described above. The organic phase from the extraction with aqueous sodium hydroxide to remove DHP and HHP was washed with water, dried with 4A° sieves, and flash distilled in a Rinco evaporator to remove approximately 20% of the unreacted DIPB from the recycle stream. The flash distillate was found to contain as much as 30% MHP and a smaller quantity of MCL by GLC analysis.

The aqueous sodium hydroxide solution containing the sodium salts of DHP and HHP was extracted with MIBK to recover DHP and HHP fraction.

Results are shown in Table VII.

EXAMPLE 7

Hydroperoxidation of m-DIPB

Containing 1.2% o-DIPB, with a 100% Recycle

Hydroperoxidation of each cycle was made with 350 g fresh DIPB feed and recycle MHP-DIPB mixture. After the hydroperoxidation, the product was extracted twice with equal weights of 4% aqueous sodium hydroxide to ensure a more complete extraction of m-DHP. The concentration of m-DHP in the recycle stream was determined to be less than 1%. The aqueous sodium hydroxide solution containing the sodium salts of m-DHP and m-HHP was extracted twice at 80° C. with twice its volume of MIBK to extract back m-DHP and m-HHP. After evaporation of MIBK solvent, the product was analyzed by HPLC.

Results are shown in Table VIII.

EXAMPLE 8

Hydroperoxidation of Commercial m-DIPB with an 80% Recycle of Recovered m-MHP and m-DIPB A 5-gallon sample of commercial m-DIPB was obtained and used without any treatment. Analysis of the commercial m-DIPB by GLC indicated a 98% purity of m-DIPB. Major impurities were: 0.8% o-DIPB, 0.4% p-DIPB, and less than 0.2% trimethylindane. A technical data sheet supplied by the manufacturer showed: <96% m-DIPB, 1.5% o-DIPB, and 0.5% p-DIPB.

Hydroperoxidation was made with 350 g feed consisting of about 30 mol % fresh DIPB, 25 mol % recycle DIPB and 45–50 mol % recycle MHP, and smaller amounts of MCL, HHP and OLCL. The product was extracted twice with equal weights of (approximately 400 ml) 4% aqueous sodium hydroxide to remove DHP and HHP. The organic phase was washed with 100 ml water, dried with 35 ml 4A° sieves, and filtered. Samples of the MHP/DIPB recycle were analyzed by HPLC.

The aqueous sodium hydroxide solution was extracted twice at 80° C. with twice its volume of MIBK (800 ml each) to recover the DHP/HHP product. The MHP/DIPB recycle was flash distilled in a Rinco evaporator to remove about 20% of unreacted DIPB from each recycle. The results are shown in Table IX.

TABLE VII

DHP/HHP From m-DIPB Containing 1.2% o-DIPB, 80% Recycle

| | Conditions | | | DHP/HHP | | MHP/DIPB Recycle | | |
|---|---|---|---|---|---|---|---|---|
| Recycle No. | time hrs. | temp. °C. | MHP[1] % | wt g | DHP[1] % | wt g | MHP[1] % | % o-in DIPB |
| 0 | 40 | 87–89 | 80.1 | 76.4 | 84.7 | 281 | 61.1 | N.D.[3] |
| 1 | 24 | 86–87 | 78.0 | 66.3 | 80.8 | 307 | 53.4 | N.D.[3] |
| 2 | 24 | 86–87 | 73.4 | 64.4 | 76.7 | 308 | 56.7 | N.D.[3] |
| 3 | 24 | 86–87 | 78.8 | 69.9 | 81.9 | 304 | 57.6 | N.D.[3] |
| 4 | 24 | 86 | 60.5 | 49.6 | 62.7 | 318 | 45.9 | N.D.[3] |
| 5 | 24 | 85 | 54.4 | 47.2 | 68.7 | 314 | 43.9 | N.D.[3] |
| 6 | 24 | 85 | 63.0 | 55.7 | 75.5 | 314 | 48.3 | N.D.[3] |
| 7 | 24 | 85 | 69.9 | 63.3 | 76.9 | 308 | 52.3 | N.D.[3] |
| 8 | 24 | 85 | 76.3 | 66.9 | 82.1 | 304 | 56.7 | N.D.[3] |
| 9 | 24 | 85 | 75.1 | 68.4 | 80.7 | 303 | 52.7 | N.D.[3] |
| 10 | 24 | 85 | 78.1 | 60.3 | 83.0 | 311 | 60.3 | 4.5 |
| Av. 1–10 | | | 70.8 | 61.2 | 76.9 | 309 | 52.8 | |

| | Conditions | | DIPB | Net Production[2] | | |
|---|---|---|---|---|---|---|
| Recycle No. | time hrs. | temp. °C. | Conv.[2] % | DHP Mol % | HHP Mol % | DHP/DHP + HHP % |
| 0 | 40 | 87–89 | 63.6 | 14.0 | 4.0 | 77.8 |
| 1 | 24 | 86–87 | 50.1 | 9.7 | 3.2 | 75.2 |
| 2 | 24 | 86–87 | 44.3 | 9.6 | 3.2 | 75.0 |
| 3 | 24 | 86–87 | 50.3 | 11.4 | 4.4 | 72.2 |
| 4 | 24 | 86 | 42.6 | 4.9 | 2.9 | 62.8 |
| 5 | 24 | 85 | 30.1 | 4.8 | 2.7 | 64.0 |
| 6 | 24 | 85 | 44.9 | 7.7 | 4.0 | 65.8 |
| 7 | 24 | 85 | 46.8 | 8.8 | 4.2 | 67.7 |
| 8 | 24 | 85 | 46.4 | 10.4 | 3.1 | 77.0 |
| 9 | 24 | 85 | 47.2 | 10.6 | 3.1 | 77.4 |
| 10 | 24 | 85 | 41.7 | 9.3 | 2.8 | 76.9 |
| Av. 1–10 | | 85 | 44.4 | 8.72 | 3.36 | 72.2 |

[1]By iodometric titration.
[2]Calculated from HPLC analysis.
[3]Not determined.

TABLE VIII

DHP/HHP From m-DIPB Containing 1.2% o-DIPB, 100% Recycle

| | Conditions | | | DHP/HHP | | MHP/DIPB Recycle | | |
|---|---|---|---|---|---|---|---|---|
| Recycle No. | time hrs. | temp. °C. | MHP[1] % | wt g | DHP[1] % | wt g | MHP[1] % | % o-in DIPB |
| 0 | 40 | 85–87 | 78.1 | 65.6 | 83.2 | 283 | 55.0 | N.D.[3] |
| 1 | 24 | 85–87 | 81.2 | 70.0 | 82.9 | 302 | 62.1 | N.D.[3] |
| 2 | 24 | 87 | 70.6 | 60.5 | 75.5 | 305 | 54.0 | N.D.[3] |

TABLE VIII-continued

DHP/HHP From m-DIPB Containing 1.2% o-DIPB, 100% Recycle

| | | | | | | | | |
|---|---|---|---|---|---|---|---|---|
| 3 | 24 | 87-89 | 70.4 | 62.3 | 76.5 | 304 | 53.4 | N.D.[3] |
| 4 | 24 | 89 | 64.8 | 63.1 | 70.0 | 303 | 52.1 | N.D.[3] |
| 5 | 24 | 87-88 | 62.1 | 67.5 | 71.4 | 298 | 50.8 | N.D.[3] |
| 6 | 24 | 87 | 64.3 | 65.3 | 70.7 | 301 | 49.8 | N.D.[3] |
| 7 | 24 | 87 | 64.1 | 63.4 | 67.2 | 300 | 49.3 | N.D.[3] |
| 8 | 24 | 87 | 55.1 | 58.2 | 62.8 | 305 | 44.7 | N.D.[3] |
| 9 | 32 | 85-87 | 36.1 | 47.4 | 32.9 | 310 | 28.5 | 9.3 |
| Av. 1-7 | | | | 68.2 | 64.6 | 73.5 | 302 | 53.1 |
| Av. 1-9 | | | | 63.2 | 62.0 | 67.8 | 303 | 49.4 |

| | Conditions | | DIPB | Net Production[2] | | |
|---|---|---|---|---|---|---|
| Recycle No. | time hrs. | temp. °C. | Conv.[2] % | DHP Mol % | HHP Mol % | DHP/DHP + HHP % |
| 0 | 40 | 85-87 | 63.2 | 12.0 | 3.3 | 78.4 |
| 1 | 24 | 85-87 | 46.8 | 11.5 | 3.7 | 75.7 |
| 2 | 24 | 87 | 39.9 | 8.2 | 4.3 | 65.6 |
| 3 | 24 | 87-89 | 40.8 | 8.6 | 4.7 | 64.7 |
| 4 | 24 | 89 | 44.4 | 7.8 | 6.0 | 56.5 |
| 5 | 24 | 87-88 | 47.0 | 7.8 | 5.9 | 56.9 |
| 6 | 24 | 87 | 43.2 | 7.5 | 6.0 | 55.6 |
| 7 | 24 | 87 | 46.5 | 6.5 | 5.1 | 48.2 |
| 8 | 24 | 87 | 44.3 | 4.5 | 4.7 | 48.9 |
| 9 | 32 | 85-87 | 40.2 | 2.3 | 2.1 | 52.3 |
| Av. 1-7 | | | 44.1 | 8.27 | 5.10 | 61.9 |
| Av. 1-9 | | | 43.7 | 7.19 | 4.72 | 60.4 |

[1]By iodometric titration.
[2]Calculated from HPLC analysis.
[3]Not determined.

TABLE IX

DHP/HHP From Commercial m-DIPB, 80% Recycle

| | Conditions | | DHP/HHP | | | MHP/DIPB Recycle | | |
|---|---|---|---|---|---|---|---|---|
| Recycle No. | time hrs. | temp. °C. | MHP[1] % | wt g | DHP[1] % | wt g | MHP[1] % | % o-in DIPB |
| 0 | 40 | 85-86 | 71.2 | 75.6 | 81.4 | 280 | 60.3 | N.D.[4] |
| 1 | 24 | 85 | 67.9 | 48.7 | 82.1 | 319 | 56.0 | 3.0 |
| 2 | 24 | 85 | 72.8 | 59.2 | 83.6 | 314 | 58.8 | 3.3 |
| 3 | 32 | 85 | 86.0 | 74.4 | 86.9 | 303 | 62.6 | 4.2 |
| 4 | 32 | 85 | 80.2 | 72.2 | 84.8 | 300 | 61.6 | 4.0 |
| 5 | 32 | 85 | 81.4 | 73.4 | 85.1 | 302 | 61.7 | 5.2 |
| 6 | 32 | 85 | 75.2 | 75.8 | 84.6 | 298 | 60.4 | 5.4 |
| 7 | 32 | 85 | 81.1 | 76.3 | 84.9 | 298 | 59.7 | 5.1 |
| 8 | 32 | 85 | 83.4 | 81.8 | 83.1 | 305 | 59.9 | 4.6 |
| 9 | 32 | 85 | 78.1 | 76.6 | 84.9 | 296 | 58.9 | 4.3 |
| Av. 1-9 | | | 78.5 | 70.9 | 84.4 | 304 | 60.0 | 4.3 |

| Recycle No. | Conditions | | DIPB Conv.[2] % | Net Production[2] | | | Yield[3] % |
|---|---|---|---|---|---|---|---|
| | time hrs. | temp. °C. | | DHP Mol % | HHP Mol % | DHP/DHP + HHP % | |
| 0 | 40 | 85-86 | 75.6 | 15.3 | 3.0 | 83.6 | 93.4 |
| 1 | 24 | 85 | 34.2 | 7.2 | 2.4 | 75.0 | 92.3 |
| 2 | 24 | 85 | 45.0 | 8.9 | 3.6 | 71.2 | 94.7 |
| 3 | 32 | 85 | 65.8 | 14.7 | 3.7 | 79.9 | 92.0 |
| 4 | 32 | 85 | 50.5 | 10.3 | 3.9 | 72.5 | 95.3 |
| 5 | 32 | 85 | 57.9 | 12.7 | 4.1 | 75.6 | 93.9 |
| 6 | 32 | 85 | 53.1 | 11.3 | 4.0 | 73.9 | 95.6 |
| 7 | 32 | 85 | 52.2 | 12.3 | 4.5 | 73.2 | 87.5 |
| 8 | 32 | 85 | 54.9 | 13.2 | 3.7 | 78.1 | 90.9 |
| 9 | 32 | 85 | 52.9 | 11.6 | 4.2 | 73.4 | 92.4 |
| Av. 1-9 | | 85 | 51.8 | 11.4 | 3.8 | 75.0 | 92.8 |

[1]By iodometric titration.
[2]Calculated from HPLC analysis.
[3] $\frac{\text{Mol DHP} + \text{Mol HHP} \times 100}{\text{DIPB conv.} - \text{Mol MHP} - \text{Mol MC}}$
[4]Not determined.

Hydroperoxidation of m-DIPB containing 1.2% o-isomer with 80% recycle of unreacted DIPB produced encouraging results as shown in Table VII. As the recycles progressed the decreases in % final MHP was less significant and the average weight of the DHP/HHP fraction was 61.2 g for the 10 cycles. More importantly, the average % DHP by titration of the DHP/HHP fraction was 76.9%, compared to 67.8% for the 100% recycle series, as shown in Table VIII. Diverting 20% of the recycle DIPB was observed to have raised the % DHP in the DHP/HHP product nearly 10%.

The MHP-DIPB fraction recovered from Recycle 9 (See Table VIII) was distilled to recover unreacted m-DIPB. Analysis of the recovered m-DIPB by GLC. showed it to have 9.3% o-isomer and 4.8% 1,1,3-trimethylindane (TMI) as impurities. It supports the conclusion that the deterioration in m-DIPB hydroperoxidation with increasing recycles is caused by the build-up of o-DIPB concentration in the recycles. Similarly, the mol % DHP/DHP+HHP determined by HPLC was 72.2%, compared to 60.4%. Therefore, it is concluded that hydroperoxidation with 80% recycle of DIPB produces higher selectivity to desirable hydroperoxides (DHP+HHP).

It was concluded, based on the data of Examples 6 and 7, that m-DIPB is hydroperoxidized to a 3:1 mixture of m-DHP/m-HHP product in about 95% selectivity in a cyclic batch operation at 85° C. and 1 atm, at a DIPB conversion of 45-55% per cycle, provided the concentration of o-isomers in the recycle is kept below about 6%.

In the cyclic batch hydroperoxidation of Example 8 using commercial m-DIPB, a feed containing 50 mol % m-DIPB, 40 mol % MHP, 5 mol % MCL, and 2.5 mol % was oxidized to produce 25 mol % of m-DHP/m-HHP product and 25 mol % unreacted m-DIPB of the 25 mol % recovered DIPB, 20 mol % was recycled to the hydroperoxidation and 5 mol % was removed for returning to the manufacturer. Results shown in Table IX show that there was practically no change in final MHP concentration after nine cycles of hydroperoxidation. The slight variation in final MHP concentration was probably caused by temperature fluctuation since a constant temperature bath was not used. Neither the DHP concentration of DHP/HHP fraction determined by titration nor the value of % DHP/DHP+HHP determined by HPLC analysis changed very much with the number of recycles. Most importantly, the concentration of o-DIPB in the recycle DIPB stream remained in the range of 3.0 to 5.4%, well below the maximum allowable impurity level of 6.0%. In other words, hydroperoxidation of m-DIPB is not deteriorated unless there is a build-up of o-DIPB concentration in the recycle stream. The average yield of DHP/HHP product was 92.8% calculated from the equation:

$$\text{Yield} = \frac{\text{Mol } DHP + \text{Mol } HHP \times 100}{DIPB \text{ conv.} - \text{Mol } MHP - \text{Mol } MCL}$$

The m-DHP product is produced in good yield by the process of the present invention for use in the preparation of resorcinol and acetone.

What is claimed is:

1. A process for the preparation of m-diisopropylbenzene dihydroperoxide comprising oxidizing diisopropylbenzene which is comprised of m-diisopropylbenzene and less than 6% o-diisopropylbenzene under anhydrous, non-alkaline conditions with oxygen.

2. The process recited in claim 1 further comprising extracting a mixture of m-diisopropylbenzene dihydroperoxide and m-diisopropylbenzene hydroxyhydroperoxide from the products of said oxidizing step;
    removing about 20% of the products remaining after said oxidizing and extracting steps; and
    recycling about 80% of the products remaining after the oxidizing and extracting steps to a feed stream of said diisopropylbenzene for use in repeating said oxidizing step.

3. The process recited in claim 1 wherein the temperature of said oxidizing step is about 85° C.-95° C.

* * * * *

UNITED STATES PATENT AND TRADEMARK OFFICE
CERTIFICATE OF CORRECTION

PATENT NO. : 4,935,551
DATED : June 19, 1990
INVENTOR(S) : CHING-YONG WU

It is certified that error appears in the above-identified patent and that said Letters Patent is hereby corrected as shown below:

Column 10, line 51 in the drawing, "CH₂" should be --CH₃--.

Column 11, line 2 in the drawing, "CH₂" should be --CH₃--.

Column 18, line 65, the period "." after "GLC" should be deleted.

Column 19, line 19, a period --.-- should be inserted after "m-DIPB", and "of" should be --Of--.

Signed and Sealed this

Twenty-eighth Day of December, 1993

Attest:

BRUCE LEHMAN

*Attesting Officer*  *Commissioner of Patents and Trademarks*